United States Patent [19]

Waterstrat

[11] Patent Number: 5,019,337
[45] Date of Patent: May 28, 1991

[54] DUCTILE INTERMETALLIC COMPOUNDS FOR DENTAL APPLICATIONS

[75] Inventor: Richard M. Waterstrat, Gaithersburg, Md.

[73] Assignee: American Dental Association Health Foundation, Gaithersburg, Md.

[21] Appl. No.: 480,727

[22] Filed: Feb. 16, 1990

[51] Int. Cl.$^5$ .................. C22C 16/00; C22C 5/04; C22C 30/00

[52] U.S. Cl. .................... 420/580; 148/421; 148/430; 148/442; 420/422; 420/462; 420/463; 420/466

[58] Field of Search ............... 420/422, 462, 463, 466, 420/580; 148/400, 421, 425, 426, 429, 430, 437, 442

[56] References Cited

U.S. PATENT DOCUMENTS

| | | | |
|---|---|---|---|
| 3,660,082 | 5/1972 | Negishi et al. | 420/580 |
| 4,040,129 | 8/1977 | Steinemann et al. | 3/1.9 |
| 4,294,608 | 10/1981 | Sedlak et al. | 420/466 |
| 4,482,323 | 11/1984 | Schaffer | 433/207 |
| 4,551,302 | 11/1984 | Wagner et al. | 420/464 |
| 4,576,789 | 3/1986 | Prasad | 420/464 |
| 4,576,790 | 3/1986 | Rothaut et al. | 420/464 |
| 4,591,483 | 5/1986 | Nawaz | 420/463 |
| 4,608,229 | 8/1986 | Lanam et al. | 420/464 |
| 4,865,663 | 9/1989 | Tuominen et al. | 148/430 |

FOREIGN PATENT DOCUMENTS 60-224727 11/1985 Japan .................... 420/422

OTHER PUBLICATIONS

Hossain, Harris, and Barraclough, "A Study of ZrCo and Related Ternary Phases Represented by the General Formula, $Zr_{50}Co_{50-x}Ni_x$," *Journal of the Less-Common Metals*, 37 (1974), 35–57.

C. Lall, M. H. Loretto and I. R. Harris, "Transformation and Deformation Studies of Some Zr (CoNi) Alloys," *Acta Metall.*, 1978, 1631–1641.

Victor F. Zackay, Earl R. Parker, Dieter Fahr and Raymond Busch, "The Enhancement of Ductility in High-Strength Steels", *Transactions of the AMS*, 1967, 252–259.

*Primary Examiner*—R. Dean
*Assistant Examiner*—Robert R. Koehler
*Attorney, Agent, or Firm*—Allegretti & Witcoff, Ltd.

[57] ABSTRACT

Alloys suitable for dental or medical devices are disclosed. A typical alloy comprises about 35 to about 60% by weight of zirconium, about 1 to about 60% by weight of palladium and about 1 to about 60% by weight of ruthenium.

17 Claims, No Drawings

DUCTILE INTERMETALLIC COMPOUNDS FOR DENTAL APPLICATIONS

BACKGROUND OF THE INVENTION

1. Field of the Invention

This invention was supported by grants from the American Dental Association Health Foundation (ADAHF) and The National Institute of Dental Research (NIH).

This invention relates to alloy compounds which undergo stress-induced martensitic transformations at or near mouth or body temperature. A martensitic transformation occurs in these alloys when they transform under stress from a cubic CsCl or B2 type structure, which is stable at elevated temperatures, to a CrB type structure that is stable at a lower temperature. This type of transformation increases the ductility of these alloys. Ductility, as used hereinafter, is defined as the ability of a material to deform plastically without fracturing as measured by elongation or reduction of area in a tensile test. More specifically, the present invention relates to new alloys exhibiting adequate strength for use in dental or medical implants or protheses and enhanced ductility as compared to the known cubic CsCl or B2 type alloys which do not transform. The alloys of the present invention are composed of elements comprising zirconium and/or, optionally, those others in Group IVB of the periodic table, together with selected elements of Groups VIII, IIIA and IVA, most preferably palladium and ruthenium. The adequate strength and enhanced ductility of the new alloys make them suitable for use in the dental or medical areas as for example, castings for crowns, bridges, dental or medical implants or as prosthetic devices.

2. Description of the Prior Art

Methods of enhancing the ductility of high strength steels and other alloys, through a combination of elements enabling the formation of stress-induced martensitic structures appear in the prior art. See for example, Zackay, V.F., Parker, E.R., Fahr, D., and Busch, R., "The Enhancement of Ductility in High Strength Steels", *Trans. Asm.* 60 252-259 (1967). For examples of zirconium-cobalt-nickel alloys see Lall, C., Loretto, M.H., and Harris, I.R., "Transformation and Deformation Studies of Some Zr(CoNi) Alloys", *Acta Met.* 26 1631-1641 (1978) and Barraclough, K.G., Hossain, D., and Harris, I.R., "A Study of ZrCo and Related Ternary Phases Represented by the General Formula $Zr_{50}Co_{50-x}Ni_x$.", 37 *Journal of the Less Common Metals* 35-57 (1974).

Numerous alloys have been used in the dental and medical areas for firing on dental porcelain, in making porcelain jacketed dental restorations, as cast alloys for removable dental construction, or for use in making surgical implants, see for example, Prasad U.S. Pat. No. 4,576,789, Wagner et al. U.S. Pat. No. 4,551,302, Schaffer U.S. Pat. No. 4,482,323, Nawaz U.S. Pat. No. 4,591,483, Lanam et al. U.S. Pat. No. 4,608,229, Rothaut et al. U.S. Pat. No. 4,576,790 and Steinemann et al. U.S. Pat. No. 4,040,129. The present invention distinguishes itself over the prior art in the number and type of elements composing the alloy and the percent composition of the elements. For example, applicant's alloy contains significantly less palladium than the 60% used by Lanam et al. in the '229 patent. Applicant's alloy further distinguishes itself from Prasad's '789 patent by containing no copper and significantly less palladium than the 70% disclosed in Prasad. Also, applicant's alloy distinguishes itself from the Wagner et al. '302 patent by having no platinum, gold, etc. and significantly less palladium than the 65% suggested therein. The instant alloy further distinguishes itself from Schaffer's '323 patent by containing no silver, tin, etc. and significantly less palladium than the 45% used in Schaffer. Finally, the alloy of the invention distinguishes itself from Steinemann et al. by containing no niobium, tantalum, chromium, molybdenum or aluminum and distinguishes itself from Nawaz and Rothaut et al. by containing no gold.

SUMMARY OF THE INVENTION

The present invention comprises alloy compositions that possess adequate strength for dental and medical implants and protheses and greatly enhanced ductility as compared to nontransforming CsCl or B2 type alloys due to stress induced martensitic transformations within the alloy. The alloy consists essentially of zirconium and other elements in Group IVB of the periodic table together with selected elements of Groups VIII, IIIA and IVA most preferably palladium and ruthenium. The new alloy compositions are useful in dental and medical implants and prosthetic devices because of their biocompatibility with body tissue.

DETAILED DESCRIPTION OF THE INVENTION

The alloys of the present invention consist essentially of about 35 to about 60% by weight zirconium, about 1 to about 60% palladium and about 1 to about 60% ruthenium. The zirconium may be substituted entirely or in part by titanium or hafnium, whereas the palladium may be substituted entirely or in part by rhodium, iridium, platinum, aluminum or silicon. The ruthenium may be substituted entirely or in part by osmium or cobalt.

Preferred weight composition include about 46% zirconium, about 41% palladium and about 13% ruthenium or about 47% zirconium, about 36% palladium and about 17% ruthenium.

In a typical practice of the present invention, the alloys are prepared by melting the elements in an arc furnace to temperatures of approximately 1800° C. under an atmosphere of either argon or helium.

A typical commercial embodiment of the alloy is characterized by the preferred weight compositions previously mentioned.

In use, the selected alloy according to the present invention is melted in an arc furnace at the melting temperature e.g., 1800° C., under an atmosphere of argon or helium. The molten product is then cast into a mold for the desired shape of the medical or dental implant or prosthetic device to be fabricated.

What is claimed is:

1. An alloy composition having a cubic CsCl or B2 type structure which can undergo stress-induced martensitic transformations at or near mouth or body temperature and consisting essentially of about 35 to about 60% by weight zirconium, about 1 to about 60% palladium, and about 1 to about 60% ruthenium.

2. An alloy composition having a cubic CsCl or B2 type structure which can undergo stress-induced martensitic transformations at or near mouth or body temperature and consisting essentially of about 35 to about 60% by weight of a first element selected from Group IVB of the periodic table, about 1 to about 60% by weight of a second element selected from the group consisting of the elements from Group VIII excluding nickel, Group IIIA and Group IVA of the periodic table, and about 1 to about 60% by weight of a third element selected from Group VIII excluding nickel of the periodic table.

3. An alloy as defined in claim 2 wherein said first element is titanium.

4. An alloy as defined in claim 2 wherein said first element is hafnium.

5. An alloy as defined in claim 2 wherein said second element is rhodium.

6. An alloy as defined in claim 2 wherein said second element is platinum.

7. An alloy as defined in claim 2 wherein said second element is platinum.

8. An alloy as defined in claim 2 wherein said second element is aluminum.

9. An alloy as defined in claim 2 wherein said second element is silicon.

10. An alloy as defined in claim 2 wherein said third element is osmium.

11. An alloy as defined in claim 2 wherein said third element is cobalt.

12. An alloy as defined in claim 1 wherein there is by weight approximately 46% zirconium, 41% palladium and 13% ruthenium.

13. An alloy as defined in claim 1 wherein there is by weight approximately 47% zirconium, 36% palladium and 17% ruthenium.

14. An alloy composition having a cubic CsCl or B2 type structure which can undergo stress-induced martensitic transformations at or near mouth or body temperature and consisting essentially of about 35 to about 60% by weight of a first element selected from the group consisting of zirconium, titanium and hafnium, about 1 to about 60% of a second element selected from the group consisting of palladium, rhodium, iridium, platinum, aluminum and silicon, about 1 to about 60% of a third element selected from the group consisting of ruthenium, osmium and cobalt.

15. An alloy as defined in claim 2 wherein said first element is zirconium.

16. An alloy as defined in claim 2 wherein said second element is palladium.

17. An alloy as defined in claim 2 wherein said third element is ruthenium.

* * * * *